(12) United States Patent
Dorn

(10) Patent No.: US 9,161,853 B2
(45) Date of Patent: Oct. 20, 2015

(54) DELIVERY SYSTEM FOR A SELF-EXPANDING IMPLANT

(75) Inventor: Jurgen Dorn, Neulussheim (DE)

(73) Assignee: C.R. Bard, Inc., Murray Hill, NJ (US)

( * ) Notice: Subject to any disclaimer, the term of this patent is extended or adjusted under 35 U.S.C. 154(b) by 386 days.

(21) Appl. No.: 13/704,579

(22) PCT Filed: Jun. 10, 2011

(86) PCT No.: PCT/EP2011/059677
§ 371 (c)(1),
(2), (4) Date: Dec. 14, 2012

(87) PCT Pub. No.: WO2011/160965
PCT Pub. Date: Dec. 29, 2011

(65) Prior Publication Data
US 2013/0090716 A1    Apr. 11, 2013

(30) Foreign Application Priority Data
Jun. 25, 2010 (GB) .................................. 1010766.2

(51) Int. Cl.
| *A61F 2/06* | (2013.01) |
| *A61F 2/966* | (2013.01) |
| *A61F 2/00* | (2006.01) |
| *A61F 2/962* | (2013.01) |
| *A61F 2/97* | (2013.01) |

(52) U.S. Cl.
CPC .............. *A61F 2/966* (2013.01); *A61F 2/0095* (2013.01); *A61F 2/962* (2013.01); *A61F 2/97* (2013.01)

(58) Field of Classification Search
CPC ............. A61F 2/95; A61F 2/966; A61F 2/97; A61F 2002/9511; A61F 2002/011
USPC ......... 606/108, 191, 194, 198, 200; 623/1.11, 623/1.12, 1.23
See application file for complete search history.

(56) References Cited

U.S. PATENT DOCUMENTS

| 2002/0099431 A1 | 7/2002 | Armstrong et al. | |
| 2005/0004647 A1* | 1/2005 | Bassoe ......................... | 623/1.11 |
| 2012/0059448 A1* | 3/2012 | Parker et al. ................. | 623/1.11 |

FOREIGN PATENT DOCUMENTS

| EP | 1508313 B1 | 12/2008 |
| WO | 9807387 A1 | 2/1998 |

OTHER PUBLICATIONS

PCT/EP20111059677 filed Jun. 10, 2011 International Preliminary Report on Patentability dated Sep. 13, 2012.

* cited by examiner

*Primary Examiner* — Katherine M Shi
(74) *Attorney, Agent, or Firm* — Buchalter Nemer, PLC

(57) ABSTRACT

The present disclosure provides a delivery system for a self-expanding implant (31) which includes a sheath (41, 42) which surrounds and constrains the implant prior to delivery and a confining element (80) which surrounds the sheath during storage. The confining element preferably includes elongate members (81) running axially along the sheath, which compress the sheath and the stent to reduce hoop stress in the system without promoting undesired adhesion between layers of the sheath.

13 Claims, 3 Drawing Sheets

DELIVERY SYSTEM FOR A SELF-EXPANDING IMPLANT

This application is a U.S. national stage application under 35 U.S.C. §371 of International Application No. PCT/EP2011/059677, filed Jun. 10, 2011, claiming priority to United Kingdom Patent Application No. 1010766.2, filed Jun. 25, 2010, and to U.S. Provisional Application No. 61/358,856, filed Jun. 25, 2010, each of which is incorporated by reference in its entirety into this application.

The present invention relates to a delivery system for a self-expanding implant to line a bodily lumen, which includes a sheath to hold the implant in a radially compressed configuration prior to and until deployment in the lumen, when the sheath is withdrawn along the axis of the lumen.

Self-expanding implants such as stents and stent grafts are often delivered to a stenting site within a bodily lumen with the use of a catheter delivery system that is advanced percutaneously and transluminally. Although most stents and stent grafts are for the cardiovascular system, self-expanding implants can also be delivered transluminally to body lumens that carry bodily fluids other than blood. A stent without a coating is often called a "bare" stent. Stent grafts that carry a covering of a material such as expanded polytetrafluoroethane (ePTFE) are often called "covered" stents or "stent grafts". A self-expanding stent need not be made of metal but usually is, and that metal is usually a nickel titanium shape memory alloy commonly known as "NITINOL".

Given that a self-expanding stent will expand when freed of the constraint of the catheter delivery system, it follows that the catheter delivery system confining the stent will be subject to radially outward pressure from the confined stent, at least at body temperature 37° C. With NITINOL, the outward radial pressure dwindles to zero as the temperature of the stent is reduced to temperatures around 0° C. and below, with the austenitic crystal lattice changing, as the temperature reduces, to a martensitic crystal lattice.

Thus, at low temperatures, with the self-expanding stent in the martensitic state, the hoop stress on the sheath surrounding the stent in the delivery system will be relatively low, even to the extent of being close to zero. However, as the temperature rises towards body temperature, the radially outward pressure on the confining sheath will increase. Given that the confining sheath has to be flexible if the distal end of the catheter delivery system is to advance along a tortuous bodily lumen, it is invariably made of a synthetic polymeric material rather than metal. Such materials are subject to deformation and the deformation of polymers is a time-dependent phenomenon. Suppose that the self-expanding stent confined within its sheath is stored for a period of weeks or months, at room temperature or above. There is the possibility, perhaps likelihood, that the sheath will stretch and the stent will expand radially to some extent, during the extended period of storage.

Even more significant, in coated stents such as those made of Nitinol with an ePTFE covering, relaxation of the compacted ePTFE layer on the stent also contributes to radial distortion of the sheath.

As the quest continues for ways to deliver implants to ever-smaller diameter locations within the body, through ever-more tortuous delivery paths, the pressure on designers of implants and delivery systems to reduce to ever-smaller values the passing diameter of the distal end of the catheter system where the implant is located, continues to increase. This pressure pushes designers to think of sheath designs of ever-smaller wall thickness. The smaller the wall thickness of the sheath, the greater the difficulty of resisting the radially outward pressure imposed on the sheath by the stored implant.

One promising route to reduce yet further the wall thickness of the confining sheath is, perhaps paradoxically, to provide that the sheath has a double layer, namely, as a cylindrical sheath that doubles back on itself. It starts proximally of the implant, extends distally over the full length of the implant and then is turned back radially outwardly on itself, to continue back along the length of the implant, extending proximally, to a position proximal of the proximal end of the implant. That turned back end of the sheath, proximal of the implant, can be pulled proximally, when the time comes to release the stent. That proximal pull will draw proximally, progressively, the point along the length of the sheath where the sheath material doubles back on itself. That location where the sheath material doubles back on itself progresses proximally along the length of the implant, releasing as it goes the stent portion radially inside it, so that, when it finally reaches the proximal end of the implant, the implant is fully released into the bodily lumen.

The present invention represents a way to minimise the wall thickness of sheath material surrounding a self-expanding implant, so that the passing diameter of the distal end of a catheter-type implant delivery system can be reduced yet further.

According to the present invention there is provided in such a delivery system a confining element, preferably in the form of a sleeve, to surround the sheath during a storage period between placement of the implant within the sheath and said withdrawal of the sheath, the confining element serving to reduce the hoop stress in the sheath during said storage period and being removable from the sheath prior to advancement of the sheath into the said bodily lumen.

It will appreciated by skilled readers that, when the confining element acts to reduce the hoop stress in the sheath during the storage period this, in turn, can reduce the amount of time-dependent creep deformation of the sheath in contact with the stent during the storage period, that would otherwise tend to increase the diameter of the sheath, under pressure from the implant within it. In some cases such an increase could result in increasing the passing diameter of the distal end of the delivery system to a value higher than is needed for delivery of the implant, and higher than the minimum that can be achieved with the specific delivery system prior to any period of extended storage. In others, the increase could lead to fouling of the sheath during movement relative to other components of the delivery system.

It may be convenient to make the confining element as a sleeve of a heat-shrinkable material and shrink it around the sheath during manufacture of the delivery system. Such a shrinking step will bring the confining structure into embracing contact with the distal end of the delivery system. Thus, the microstructure of the heat shrunk material can be more resistant to creep stretching under hoop stress from the confined implant than the same material prior to being subjected to the heat shrinking step.

The proposal to put the sheath inside a sleeve is of no value unless the sleeve can easily be removed when the time comes to use the delivery system for delivering the implant. At that point, the sleeve must be removed prior to advancing the distal end of the delivery system into the body of the patient. One convenient way to strip off the sleeve is to include with the sleeve an elongate pull element that will, when it pulled in the proper direction, part the sleeve progressively, from one end of the sleeve towards the other, to release the hoop stress in the sleeve and release the sheath from the surrounding sleeve. One need only think of the way in which the clear plastic film around a packet of cigarettes is released from the cigarette packet to understand how any such elongate pull element might work. To assist the operation of the pull element in the environment of an operating theatre, the inventor contemplates providing the free end of any such pull element with a finger ring to receive a finger and serve as a pull ring to pull the pull element to part the sleeve. The inventor envisages making the sleeve of a PET material (polyethylene terephthalate) (polyethylenephthalate). The above mentioned self-expanding implant release system that relies on a sheath that doubles back on itself will work optimally only when the sheath material can slide on itself, so that the outer of the two coaxial layers of the sheath can easily slide proximally over the abluminal surface of the inner layer of the sheath. Suppose that such a doubled back sheath is confined inside a surrounding sleeve that imposes uniform pressure on all parts of the surface of the outer layer of the doubled back sheath. It is not inconceivable that there will be some tendency for the two facing layers of the sheath somehow to "stick" to each other, at least locally. Self-evidently, it is important that the confining sleeve shall not induce such adherence between the two facing layers of the sheath confined within it. Preferred embodiments of the present invention offer improved prospects to defeat any such tendency for adherence between the two layers of a roll back sheath.

Specifically, a preferred system according to the present invention will include means to establish spaced pressure relief zones interposed between the sheath and the sleeve for preferentially carrying the forces acting between the sheath and the sleeve, whereby zones of the sheath that lie between adjacent pressure relief zones are relieved of the full magnitude of said forces.

In other words, by confining to particular pressure zones the radially inward squeezing action of the sleeve on the sheath, the intervening parts of the surface area of the sheath will be spared the radially inward pressure and so the outer of the two facing layers of the sheath will not be pressed with full force against the abluminal surface of the inner of the two sheath layers. Indeed, with careful design of the sleeve system, it ought to be possible to arrange for there to be a physical gap between the abluminal surface of the inner sheath layer and the luminal surface of the outer sheath layer, in locations between two adjacent pressure zones. Skilled readers will appreciate that confinement of the full squeezing force of the sleeve on the sheath to specific spaced zones interspersed with pressure relief zones offers the possibility to neutralise any tendency for the two sheath layers to stick to each other in the pressure zones.

This is particularly the case if the pressure zones are confined to lines of contact on the abluminal surface of the outer layer of the sheath that run parallel to the axis of the sheath and implant. This is because any such line of contact, where sticking is likely to occur preferentially, runs along the length of the implant and therefore should present a minimal sticking problem when the sheath is progressively peeled backwards along the length of the implant from its distal end to its proximal end.

Specifically, suppose there are six lines of contact between the sleeve and the sheath, evenly distributed at 60° intervals around the circumference of the sheath. After the sleeve has been removed, and the sheath is pulled proximally to release the implant, we can take it that any sticking is likely to be found at one or more of those six points of contact distributed evenly around the circumference. However, when most of the circumference of the sleeve is peeling back from any sticking, such adherence as is to be found at the six points of contact is broken by shearing and so ought to provide hardly any impediment to the smooth and progressive rolling back of the sheath membrane to release the implant.

One way to provide a plurality of such lines of contact parallel with the axis of the sheath and implant is to provide between the sheath and the sleeve a plurality of elongate members, evenly distributed around the circumference of the sheath and sleeve and all parallel to the axis of the sheath and implant. It may be useful to provide such elongate members as tubes. It may be optimal to select the tube diameter and the number of tubes such that they are in close proximity, or even in contact with each other, in the annular gap between the sheath and the sleeve. In one preferred embodiment, for example, there are six such tubular elongate members, thus with their long axis at spaced intervals of 60° around the circumference of the axis of the implant. Another possibility is four tubes at 90° intervals parallel but spaced apart from each other.

Skilled readers will appreciate that there is no absolute need to have adjacent elongate members in continuous contact with each other, side-by-side, over the full length of the implant. When there are enough points of contact distributed along the length of the elongate members, at spaced intervals, there is no need for any such side-by-side contact between the spaced contact points. If spacers are used, there need be no contact at all between the adjacent elongate members. In the illustrated embodiment described below, it is shown how wall portions of elongate tubular members can be selectively removed to provide spaced points of side-by-side contact but a continuous line of contact of each elongate tubular member with the sheath confined radially within it.

It will likely be convenient and effective to provide the above-mentioned elongate members as components made of metal. It is envisaged that the extra cost to a delivery system for an implant caused by the provision of the elongate members and sleeve will be minimal in relation to the performance advantages obtainable, particularly in relation to the storage periods and temperatures that are liable to be encountered in practical day-to-day use of such implant delivery systems.

BRIEF DESCRIPTION OF THE DRAWINGS

For a better understanding of the present invention, and to show more clearly how the same may be carried into effect, reference will now be made, by way of example, to the accompanying Drawings, in which.

DETAILED DESCRIPTION

Best Mode

There now follows a description of one exemplary embodiment for putting the present invention into effect.

Figure 1:
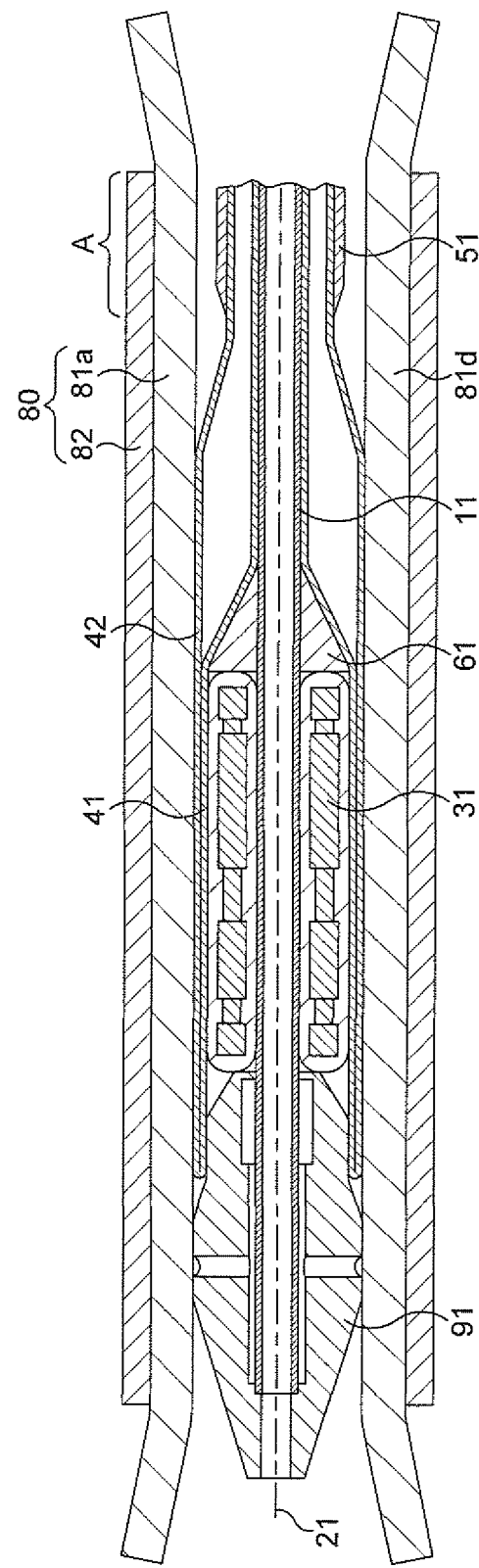
FIG. 1 is a section taken transverse to the long axis of the distal end of a delivery system for a self-expanding implant.

FIG. 1 shows a first embodiment of the present invention, being a delivery system for a self-expanding implant to line a bodily lumen. The inner components of the delivery system are essentially conventional, but will be described here to aid the reader in understanding the interaction between the various components of the system.

Defining an axis of the delivery system is inner catheter 11, which runs from a distal end of the delivery system (on the left hand side of the Figure) to a proximal end of the delivery system (not shown in the Figure but some distance beyond the right hand of the Figure).

Inner catheter 11 defines a lumen through which guide wire 21 runs. Guide wire 21 is provided to be inserted percutaneously and guided through the body passages which the stent delivery system is to navigate before the delivery system itself is introduced, in order to more easily guide the proximal end of the stent delivery system to its intended location in the body.

Coaxial with the inner catheter, and located around it in a compressed configuration is implant 31, in the present instance being a self-expanding NITINOL stent. The stent is held in a radially compressed configuration onto the inner catheter by means of inner sheath layer 41, which radially surrounds the stent and applies inwardly radial pressure thereto to maintain the stent in its compressed configuration. In the system depicted, inner sheath 41 extends distally and then folds back on itself at a distal turning point to return proximally as outer sheath 42. This configuration is conventionally known as a roll-back design, as will be explained later in terms of stent deployment.

Outer sheath 42 extends proximally until a region A, where its radius reduces to that of pull portion 51, where it attaches. Pull portion 51 extends proximally to the proximal end of the delivery system to convey an actuating tensile force from the operator to outer sheath 42. In contrast, push element 61 is provided to restrain the stent 31 from proximal axial movement relative to inner catheter 11. Accordingly, push element 61 is provided fixed in relation to inner catheter 11, in some embodiments by means of the inward pressure of inner sheath 41. Atraumatic tip 91 is provided distal of stent 31 to shield the distal end of inner sheath 41 and outer sheath 42 from the body passages through which the stent delivery system travels, and vice versa.

Figure 2:
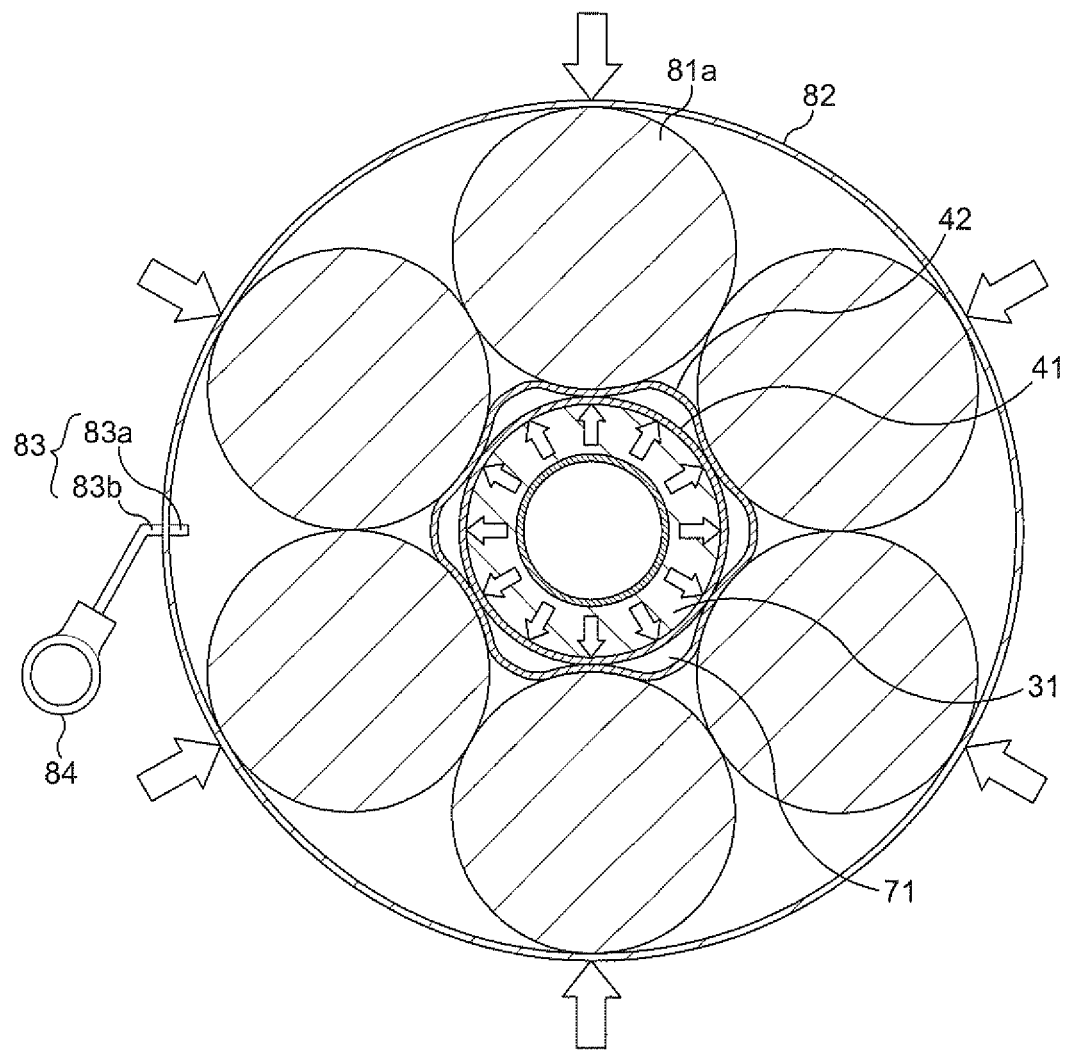
FIG. 2 is a section taken in a plane normal to the long axis of the distal end of a delivery system for a self-expanding implant.

What has been described so far is for the most part conventional. However, the embodiment shown in FIG. 1 also provides a confining structure 80, including rod members 81a, 81b, 81c, 81d, 81e and 81f, of which only 81a and 81d are shown. The rod members lie essentially parallel to inner catheter 11 at substantially equal circumferential spacings therearound and are confined themselves by sleeve 82. The radial configuration is shown in FIG. 2, in which the structures inward of outer sheath 42 have been simplified for clarity.

Confining element 82, here being a confining sleeve, provides inward radial pressure on the rods, which themselves provide inward radial pressure on outer sheath 42 at each of the six points of contact of the rods to the outer sheath around the circumference thereof. On the other hand, between the points of contact no pressure is applied. This can be seen more easily in FIG. 2, including the phenomenon of close compression of the layers 41, 42 at the contact points of the rods 81, while voids 71 exist between layers 41, 42 at regions between the points of rod circumferential contact.

By applying this radial compression to outer sheath 42, the tendency of stent 31 to distort, by virtue of its natural tendency to expand and thus apply radial pressure, inner and outer sheaths 41 and 42 is inhibited.

Prior to use in surgery, the stent delivery system is provided in the form shown in FIG. 1 in which it may be stored for an extended period.

The user, just prior to surgery, removes the confining structure 80, by, for example, splitting sleeve 82 and discarding the rods 81. The stent will then be available for use in its design-intended configuration, having dimensions and geometry undistorted over time by the aging process.

Next, the guide wire is inserted into the body percutaneously and navigated beyond the stent site. The delivery system is then directed along the guide wire to reach a particular body lumen, for example a cardiac artery. In the configuration of stent shown in the present embodiment, the pull element 51 is then retracted by application of tensile force from the proximal end of the system. The outer sheath 42 thus slides proximally over inner sheath 41 such that the folded portion distal of inner sheath 41 and outer sheath 42 progressively rolls back to expose the stent. Meanwhile, push element 61, being coupled to inner catheter 11, which is held static at the stenting site by compression forces from the proximal end of the system, restrains the stent from proximal movement to ensure accurate deployment at the intended stenting site. As the pull element is retracted, radial pressure is released on the stent and stent 31 assumes its expanded configuration, such that the inner radial void of the stent becomes larger than atraumatic tip 91, and the stent engages with the walls of the bodily lumen.

The stent delivery system may then be swiftly and easily retracted the way it arrived, leaving the stent secured in place.

Of course, many other configurations of stent delivery system than roll-back systems may be used in conjunction with confining structure 80. Indeed, confining structure 80 provides an effective means of containing any self-expanding implant delivery structure which is otherwise liable to expand over time and therefore potentially exceed its design tolerances. For example, confinement structure 80 can be used with stent delivery systems having pull-back, rather than roll-back, sheaths.

The construction of elements within confining structure 80 may be, as has been mentioned, conventional. On the other hand, the innovative confining structure 80 may itself be realised in a number of different forms. Considering the arrangement of FIGS. 1 and 2, confining structure 80 is provided as longitudinal rods spaced equidistantly about the circumference of the outer sheath 42, but other configurations to those shown in FIG. 1 are entirely possible.

For example, the rods may instead be formed as hollow cylinders and/or their arrangement and spacing around the circumference of the outer sheath may be varied. For example, four rods or eight rods may be contemplated, and their diameter varied in comparison to the diameter of the outer sheath.

In some embodiments, a split-wire 83, shown schematically in FIG. 2, may be provided, running the length of the sleeve, to enable the user to easily and swiftly split the sleeve before use, without the use of a separate tool. Such a split-wire may run distally (portion 83a) within the sleeve between two of the rods and may then loop at the distal end before returning (portion 83b) to the proximal end on the outside of the sleeve, terminating in a pull-ring 84. Pulling on the pull-ring will then cause the wire to split the outer sleeve longitudinally, distal to proximal. Thin steel wire is suitable as a split-wire, in some embodiments.

In one embodiment, the rods do not touch but approach each other closely. This permits a high degree of contact with the outer sheath and confinement thereof while preventing variations in confining force or inability to sufficiently compress due to the rods touching one to another. In another embodiment, the rods are configured to touch one another at a desired level of confining pressure or confining diameter, to prevent the inner components of the stent delivery system becoming crushed by overpressure.

In the above embodiment, the conventional stent structure lying within the confining structure, namely that lying within the radius of the outer sheath, typically has a diameter of around 2.4 mm. In such a configuration, stent diameters themselves of around 2.1 mm are conceivable, in their compressed state. Of course, in their expanded state such stents typically achieve outer diameters of around 7 mm, depending on application. For such applications, rods of the confining structure having a diameter around 2 mm may be appropriate.

As to the other components, the atraumatic tip 91 is typically formed from polyurethane, the inner catheter is typically a polyimide tube, while the inner and outer sheaths are typically formed from 80 µm-thick PET which are respectively cold drawn (for the inner sheath) and heat shrunk (for the outer sheath) to a reduced thickness during manufacture. The thickness may be reduced from an original thickness of 80 µm down to a reduced thickness of 40 µm, in one exemplary embodiment. Further details of the construction of typical roll-back stent delivery systems to which the present invention may be applied may be found in published patent applications, such as WO 2006/020028 A1.

The rods are envisaged to be made from steel or polyamide, but other materials, including both metals and polymers, are well within the choice of the skilled designer to select. However, both steel and polyamide are considered to be especially able to give the required resistance to distortion preferred in embodiments of the present invention.

Indeed, if the rods are sufficiently resistant to deformation, it may not be required to provide a sleeve running the entire length of the confining structure, but to merely provide a number of compressing ligatures spaced along the length of the rods, in the manner of the hoops used to compress a traditional barrel of beer, wine or ale. Therefore, another embodiment is possible wherein the outer sleeve is replaced by a series of rings which may be slid along the rods to release them. Alternatively, a clamshell clamping arrangement may be provided around the rods, which arrangement may be released by a catch prior to use of the delivery system.

Figure 3:
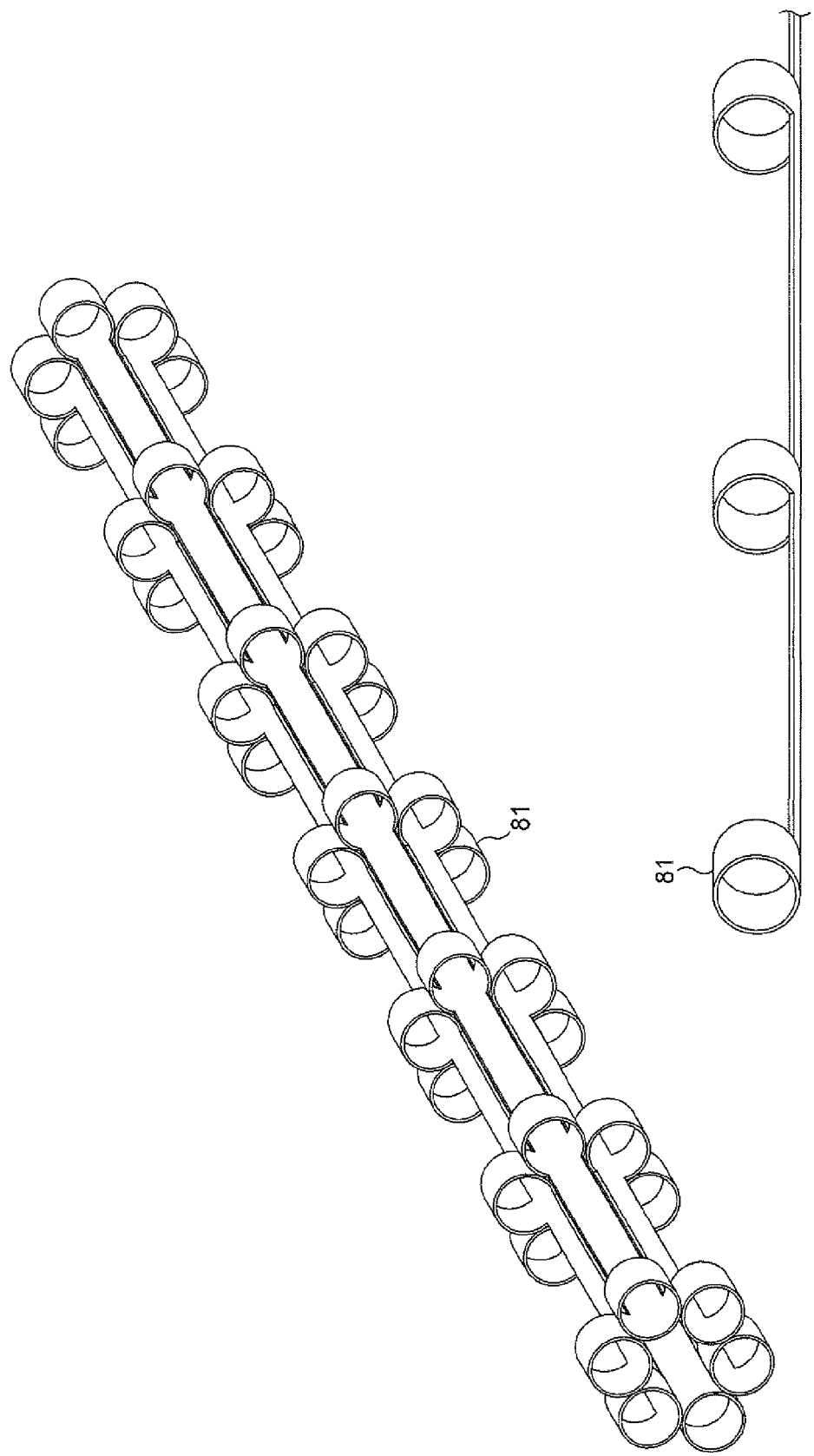
FIG. 3 is an isometric view through an assembly of elongate members applicable to the embodiment shown in section in FIG. 1 together with an example of an isolated elongate member for use in such an assembly.

Another embodiment is contemplated having a configuration of confining structure as shown in FIG. 3. FIG. 3 does not show the inner stent delivery components or the outer sleeve, but shows how a bundle of six tubes may be arranged to perform the same function as the rods 81, even though portions of the tubes have been cut out circumferentially, except for certain circumferentially intact portions spaced along the length. These uncut portions, having a complete circumference, transfer the compressive force of the sleeve through the tubes to the confined inner components of the stent delivery system. On the other hand, where the circumference is not complete, sufficient of the circumference remains to provide a line of pressure along the stent delivery components to achieve the effects of the invention. In this embodiment, the characteristics of the material from which the tubes are formed will determine how closely the full-circumference portions need to be spaced and how much of the circumference may be removed in the intervening cut-out portions. However, it is envisaged that the advantages of the present invention may be obtained even when the cut-out portions retain only around 130° of circumference each.

As to the construction of an embodiment of the complete confined delivery system, starting from a complete conventional stent delivery system, the rods are located in their predetermined positions around the conventional delivery system and heat-shrink tubing applied to the outside. This heat-shrink tubing is typically PET tubing, which will shrink radially within around five seconds when a temperature of 200° C. is applied. During manufacture of stent delivery systems, it is generally considered highly undesirable to apply heat to a region proximate to a compressed-shape memory stent, in case the memory of the expanded configuration is distorted or destroyed, leading to potential catastrophic deployment failure. However, in the described embodiment, heat-shrinking of the outer sleeve is entirely possible, since the intervening rods and air gaps provide sufficient insulation to prevent effective heat transfer to the stent during the period when the heat-shrink tube is heated to cause it to shrink and radially confine the rods.

The present invention is not limited to the presently-disclosed embodiments, but rather solely by the scope of the appended claims. The skilled reader will easily contemplate how embodiments of the confining structure may be incorporated into other constructions of implant delivery systems where dimensional creep due to aging is undesirable. Such embodiments may not be herein explicitly described, but with nevertheless be clearly within the ambit of the skilled reader without undue experimentation and without the exercise of inventive skill.

The invention claimed is:

1. A delivery system for a self-expanding implant to line a bodily lumen, which includes a sheath to hold the implant in a radially compressed configuration prior to deployment in the lumen, when the sheath is withdrawn along the axis of the lumen, the system further comprising:
   a removable assembly comprising a plurality of components surrounding the sheath until the delivery system is percutaneously inserted in a bodily lumen, wherein the plurality of components are parallel elongate members, and the plurality of components are spaced at regular intervals around the removable assembly circumference on a luminal surface of the removable assembly, wherein the elongate members are tubular; and
   spaced pressure relief zones disposed in a space between at least two parts of a component of the plurality of components and the sheath or between at least two components of the plurality of components and the sheath.

2. The system according to claim 1, wherein the assembly further comprises a sleeve.

3. The system according to claim 2, wherein the sleeve comprises a heat-shrinkable material.

4. The system according to claim 2, including an elongate pull element disposed near the sleeve and having a distal end that is mounted to or around the sleeve wherein the pull element is adapted to contact the sleeve thereby parting the sleeve progressively, from one end of the sleeve towards the other, to release the sheath from the surrounding sleeve.

5. The system according to claim 4, wherein the pull element has a free proximal end adapted to actuate the pull element to initiate contacting and parting the sleeve.

6. The system according to claim 2, wherein the sleeve comprises PET.

7. The system according to claim 1, wherein the tubular members have a circular cross-section.

8. The system according to claim 1, wherein adjacent elongate members contact each other along their length.

9. The system according to claim 8, wherein the elongate members contact each other only at predetermined regularly spaced contact zones along their length.

10. The system according to claim 9, wherein the elongate members have a constant cross-section at the contact zones and a smaller cross-section between the contact zones.

11. The system according to claim 10, wherein the elongate members comprise regions with a tubular cross-section separated by abluminally facing cut regions in which part of the tube is absent.

12. The system according to claim 1, further comprising a self-expanding implant radially compressed by the sheath and the confining element.

13. A delivery system for a self-expanding implant to line a bodily lumen, which includes a sheath to hold the implant in a radially compressed configuration prior to deployment in the lumen, when the sheath is withdrawn along the axis of the lumen, the system further comprising:

- a removable assembly comprising a plurality of components surrounding the sheath until the delivery system is percutaneously inserted in a bodily lumen; and
- spaced pressure relief zones disposed in a space between at least two parts of a component of the plurality of components and the sheath or between at least two components of the plurality of components and the sheath,
- the plurality of components are parallel, tubular elongate members, and the plurality of components are spaced at regular intervals around the assembly circumference on the assembly luminal surface,
- adjacent elongate members touch each other along their length only at predetermined regularly spaced contact zones along their length,
- the elongate members have a constant cross-section at the contact zones and a smaller cross-section between the contact zones, and
- the elongate members comprise regions with a tubular cross-section separated by abluminally facing cut regions in which part of the tube is absent.

* * * * *